United States Patent [19]

Kumagai

[11] Patent Number: 5,289,603
[45] Date of Patent: Mar. 1, 1994

[54] MEDICAL BED WITH DEVICE FOR RETAINING PATIENT

[76] Inventor: Noboru Kumagai, 150 Tomioka-cho, Sano-shi, Tochigi-ken, Japan

[21] Appl. No.: 976,148

[22] Filed: Nov. 13, 1992

[30] Foreign Application Priority Data

Jun. 26, 1992 [JP] Japan ................................ 4-44605[U]

[51] Int. Cl.$^5$ ............................................ A61G 7/06
[52] U.S. Cl. ................................................ 5/621; 5/624; 128/869
[58] Field of Search ................................ 5/621–624; 128/869, 870

[56] References Cited

U.S. PATENT DOCUMENTS

| | | | |
|---|---|---|---|
| 2,535,559 | 12/1950 | Wolf | 5/621 X |
| 2,678,857 | 5/1954 | Hans | 5/621 X |
| 3,434,165 | 3/1969 | Keane | 5/621 X |
| 3,829,079 | 8/1974 | Fox | 5/621 |
| 5,096,173 | 3/1992 | Yamashita et al. | 5/621 |

FOREIGN PATENT DOCUMENTS

| | | |
|---|---|---|
| 0186615 | 7/1986 | PCT Int'l Appl. |
| 547995 | 9/1942 | United Kingdom |
| 1301413 | 12/1972 | United Kingdom |

Primary Examiner—Michael F. Trettel

[57] ABSTRACT

Disclosed is a medical bed comprising: a bed plate on which a patient is laid in a desired posture; and a device for retaining the patient in the desired posture in such a manner that the patient is prevented from moving along the bed plate. The retaining device comprises: a plurality of elongated members for blocking motion of the patient along the bed plate; and a plurality of recessed of the bed plate or suction pad equipped to each elongated member for adjustably fitting the elongated members to the bed plate to adapt the elongated members for the desired posture of the patient.

The medical bed with the retaining device is suitable for medical treatment of patients, and in particular, for treatment of infant patients.

18 Claims, 3 Drawing Sheets

MEDICAL BED WITH DEVICE FOR RETAINING PATIENT

BACKGROUND OF THE INVENTION

1. Field of the Invention

The present invention relates to a medical bed, and in particular to a medical bed on which a patient, especially an infant patient, is laid and retained in a posture required for medical care, the bed being equipped with a device that allows the patient in a retaining posture to be adjustably set.

2. Description of the Prior Art

When a doctor or some other medical practitioner treats a patient, especially in the case of treating an infant patient, it is sometimes necessary for safety of the patient to retain the patient in a specific posture on a bed. For example, in the case of sampling cerebrospinal fluid from a patient for diagnostic analysis, the patient must be kept in a sidefacing position. However, in such a case if the patient is an infant, it often hates to keep still on the bed, and it wants to move around. As a result, two or more nurses must hold the infant patient in a fixed posture on the bed during treatment. Consequently, the assistance of several people is required in order to treat one patient. In more difficult cases, a local or general anesthetic treatment is required for keeping the patient completely still. In many circumstances like the above-mentioned case, a way has been sought to retain a patient in a desired posture on a bed through easy and simple means that can be quickly carried out by one person.

SUMMARY OF THE INVENTION

With these problems in mind, therefore, it is the primary object of the present invention to provide a novel medical bed in which it is possible to retain a patient in a desired posture in a easy and simple manner that can be quickly carried out by one person.

It is a further object of the present invention to provide a device for adjustably retaining a patient in a desired posture on the bed in accordance with the body size of the patient.

In order to achieve the above-mentioned object, a medical bed according to the present invention comprises: a bed plate on which a patient is laid in a desired posture; and means for retaining the patient in the desired posture in such a manner that the patient is prevented from moving along the bed plate.

A device for adjustably retaining a patient in a desired posture on a bed according to the present invention comprises: blocking means for blocking motion of the patient along the bed plate; and fitting means for adjustably fitting the blocking means to the bed plate to adapt the blocking means for the desired posture of the patient.

With use of the above device, a method of retaining a patient on a bed in a posture in which the patient is laid facing sideways, comprises: laying the patient on the bed plate so as to lie sideways with knees and waist bent; fitting a first elongated member on the bed plate behind the shoulders of the patient so as to abut against the upper back of the patient; fitting a second elongated member on the bed plate in front of the stomach of the patient so as to abut against the abdomen of the patient; and fitting a third elongated member on the bed plate behind the knees of the patient so as to abut against the back of the knees of the patient.

The medical bed and the retaining device described above are suitable for medical treatment of patients, and in particular, for treatment of infant patients.

BRIEF DESCRIPTION OF THE DRAWINGS

The features and advantages of the medical bed and a device for retaining a patient according to the present invention will be more clearly understood from the following description of the preferred embodiments of the present invention taken in conjunction with the accompanying drawings, in which like reference numerals designate the same or similar elements or sections throughout the figures thereof and in which.

DETAILED DESCRIPTION OF THE PREFERRED EMBODIMENTS

Figure 1:
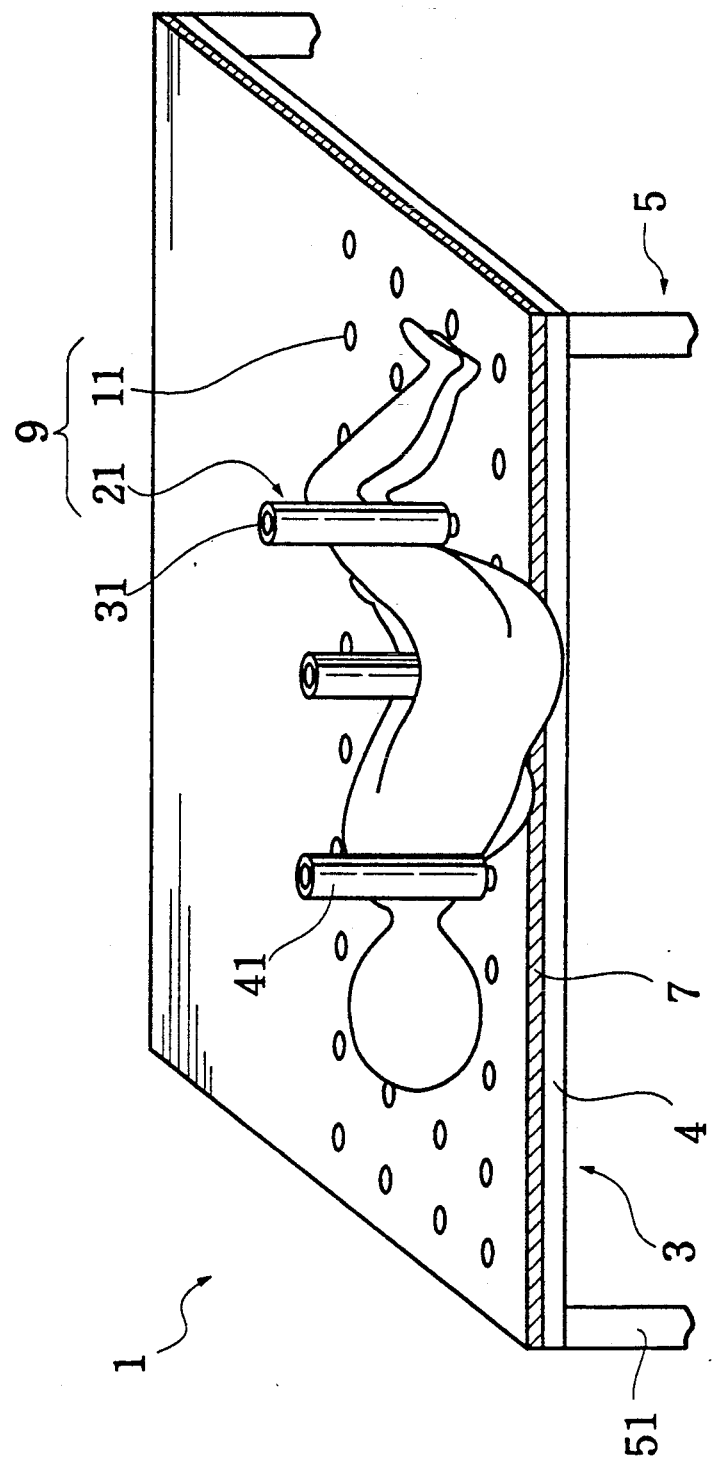
FIG. 1 is an explanatory perspective view showing an embodiment of a medical bed with a device for retaining a patient according to the present invention.

Referring now to the drawings, preferred embodiments of the medical bed and the device for retaining a patient in a predetermined posture on the bed according to the present invention will be described.

FIG. 1 is an explanatory view generally showing an embodiment of the medical bed according to the present invention. The medical bed 1 comprises a rectangular bed plate 3 including a flat board 4 which is fixed on a bedstead 5 having leg portions 51. The bed plate 3 includes an elastic pad 7 which is made of elastic material and adhered to an upper surface of the flat board 4 to cover it for absorbing shock, so that a patient can comfortably lie with no discomfort on the bed plate 3 for medical treatment. The elastic material is preferably selected from sponge, gum rubber, plastic foam and the like. If necessary, the thickness of the elastic pad can be changed, and it may also be constructed like a mattress. The elastic pad may also be omitted. The bedstead 5 is provided with strength sufficient for bearing the weight of the bed plate and the patient.

Figure 2:
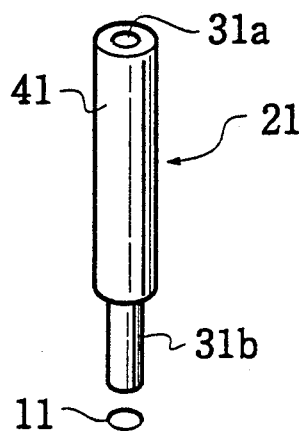
FIG. 2 is a perspective view showing the retaining device for the medical bed of FIG. 1.
Figure 3:
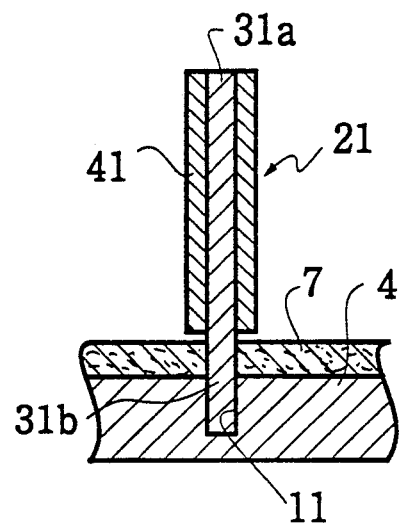
FIG. 3 is a vertical sectional view showing the retaining device of FIG. 2.

The medical bed 1 comprises a retaining device 9 for retaining the patient in a desired posture in such a manner that the patient is prevented from moving laterally along the bed plate 3. Specifically, a plurality of cylindrical recesses 11, or holes, are formed on the bed plate 3 and the elastic pad 7 so as to perpendicularly pass through the pad 7 and extend inside the flat board 4. A plurality of elongated members 21 are fitted to the recesses 11 so as to vertically stand on the bed plate 3. As shown in FIGS. 2 and 3, each elongated member 21 has a cylindrical pole 31 which has an upper blocking portion 31a and a lower fitting end portion 31b. The fitting portion 31b is removably and fittedly inserted into one of the recesses 11 of the bed plate 3 so as to firmly stand the pole 31 on the bed plate 3. Moreover, the blocking portion 31a of the pole 31 is covered with a cover 41 made of elastic material such as sponge and the like.

According to the above construction, if the elongated members 21 are mated with the appropriately selected recesses 11 so as to bring the elongated members 21 in contact with the patient who is laid in a desired posture, each of the blocking portions 31a blocks motion of the patient and thereby prevents the patient from laterally moving along the bed plate. As a result, the patient cannot laterally move past the elongated members 21 and is thus retained in the desired posture.

In the medical bed of the present invention, since the elongated members 21 can be fitted to specific positions among the many recesses 11, the elongated members 21 can be adjustably positioned in accordance with the size of the body of the patient. In this construction, if the recesses 11 are too shallow, the elongated members 21 may be jarred loose by impact, for example. Therefore, the recesses 11 preferably have sufficient depth for holding the fitting portion 31b. In the above construction, the elastic cover 41 serves as a shock absorber to reduce impact when the patient strains against the elongated members 21. This cover can also serve to prevent the patient from slipping along one or more of the elongated members 21.

The following is an example of a method of retaining an infant patient on the above-described medical bed in a posture in which the patient is laid facing sideways for sampling cerebrospinal fluid of the patient.

First, the patient is laid on the bed plate so as to lie sideways with knees and waist bent. Next, one of the elongated members is fitted in one recess which is in the rear of the scapulae of the patient so as to abut aginst the back of the patient. Then, another elongated member is fitted in another recess in front of the stomach of the patient so as to abut against the abdomen of the patient. Finally, a third elongated member is fitted in a recess behind the knees of the patient.

According to the above method of using the medical bed of the present invention, it is possible to quickly and efficiently retain the patient in the side-facing posture shown in FIG. 1.

Figure 4:
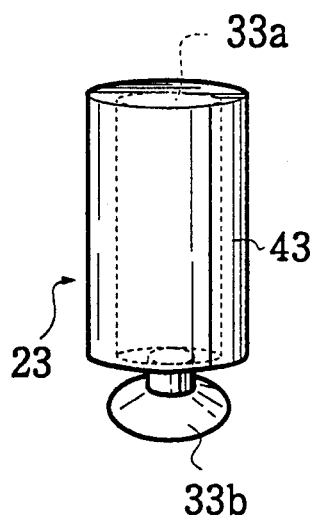
FIG. 4 is another embodiment of the retaining device according to the present invention.
Figure 5:
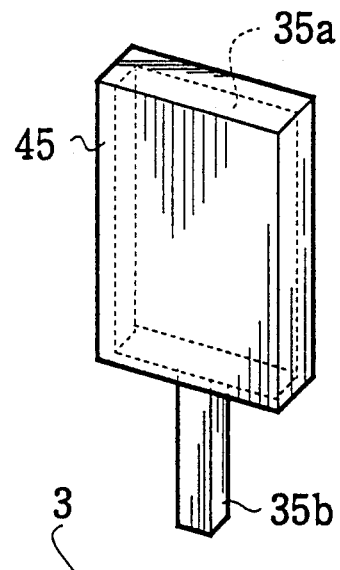
FIG. 5 is a third embodiment of the retaining device according to the present invention.
Figure 6:
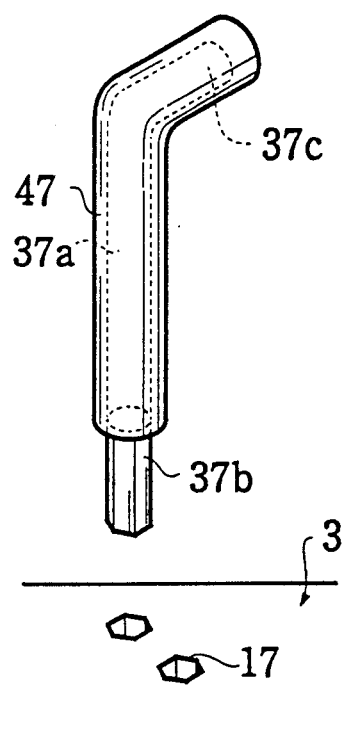
FIG. 6 is a fourth embodiment of the retaining device according to the present invention.

FIGS. 4 to 6 show modified embodiments of the retaining device according to the present invention.

As shown in FIGS. 4 and 5, it is possible to transversely extend the blocking portion of the elongate member to form a plate-like shape. In detail, the blocking portion 33a of the elongated member 23 of FIG. 4 has a transverse section like that of a convex lens, and the blocking portion 35a of FIG. 5 has a box shape. In these embodiments, each elongated member abuts the patient over a wide surface area, thereby dispersing any impact or forces exerted by the patient against the elongated member.

FIG. 4 also includes a modification of the fitting portion of the elongated member. In this embodiment, the fitting means commprises a rubber suction pad 33b coupled to the blocking portion 33a, instead of a cylindrical fitting portion. In this case, since the suction pad 33b enables the elongated member 23 to be adhered to a smooth surface, the elongated member 23 with the suction pad 33b is applicable only for a bed plate having a smooth surface with no recesses.

FIGS. 5 and 6 show other modifications of the fitting portion of the elongated member. In each of these embodiments, a side surface of the fitting portion and the corresponding side surface of the recess on the bed plate are angulated to form a regular polygonal section, respectively. Specifically, the fitting portion 35b and the recesses 15 of FIG. 5 have a squared transverse section, respectively, and the fitting portion 37b and the corresponding recess 17 of FIG. 6 have a regular hexagonal section. The above regular polygonal construction makes it possible to control the rotational position of the elongated member with respect to the longitudinal axis of the elongated member fitted to the bed plate. In FIG. 5, the rotational position of the elongated member can be changed by 90 degree increment (360/4 degrees), and that in FIG. 6 can be changed by 60 degree increments (360/6 degrees).

In addition, FIG. 6 shows an embodiment which includes an additional part, that is, a bent portion 37c. This portion can be used for preventing the patient from moving upwards relative to the bed plate.

Figure 7:
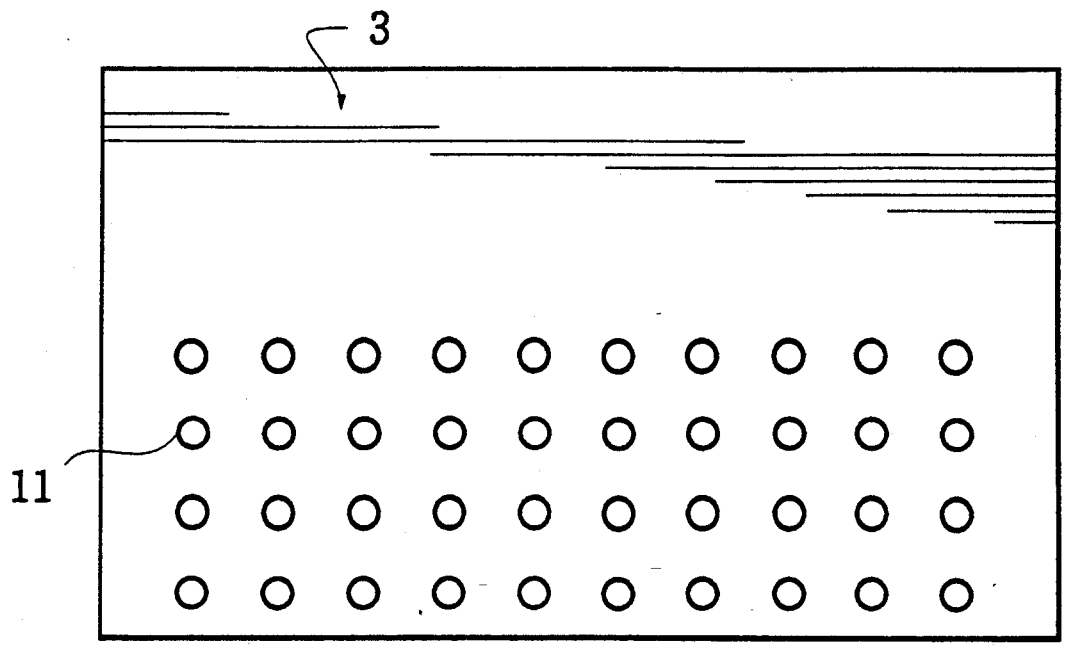
FIG. 7 is a plan view of an embodiment of the bed plate of the medical bed according to the present invention.
Figure 8:
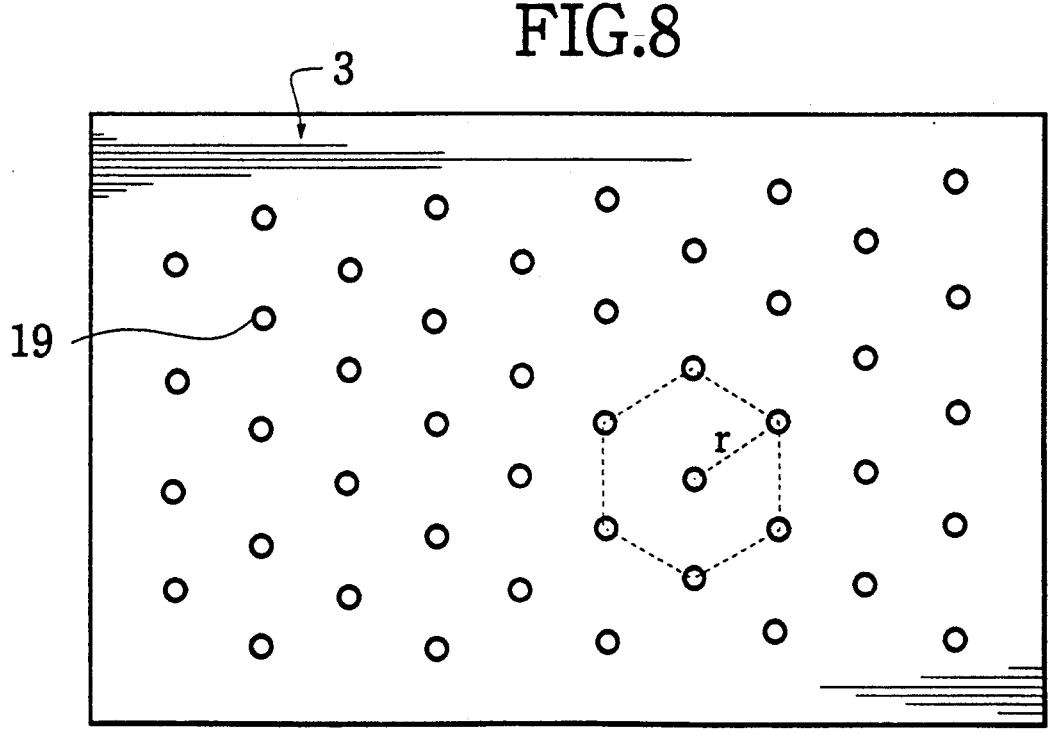
FIG. 8 is a plan view of another embodiment of the bed plate of the medical bed according to the present invention.

FIGS. 7 and 8 are plan views showing example arrangements of regularly disposed recesses in the bed plates. In FIG. 7, the spacing of the recesses 11 along the longitudinal direction of the rectangular bed plate 3 is the same as those along the transverse direction. In FIG. 8, the recesses 19 are provided in a regular hexagonal arrangement with the distance r being the same for adjacent recesses. Of the above two arrangements, the arrangement of FIG. 8 is more advantageous in regard to balanced strength of the bed plate.

Furthermore, in FIG. 7 the recesses are formed on only half of the surface of the bed plate. This allows the other half of the bed plate to be used for general purposes not requiring the retaining of a patient. On the other hand, if the fitting portions of the elongated members are thinned within the limitation of maintaining durability, the size of the recesses can be reduced as well, so that the recesses don't hinder the patient from lying comfortably. Therefore, the recesses can be disposed over the entire surface of the bed plate, as shown in FIG. 8. In the present invention, only a few elongated members are required for retaining a patient, and this number is much smaller than the number of recesses formed in the above-described arrangement. Therefore, even when elongated members are not being used, the area on the bed plate can be efficiently utilized by simply placing the elongated members in recesses along one side or near one corner of the bed plate.

In the present invention, it is possible to construct the recesses as straight or curved grooves, instead of the cylindrical holes described above, in such a manner that the elongated members can slide therealong.

Moreover, it is also possible to arrange the medical bed so that the bed plate can be inclined relative to the bedstead at a desired angle.

In addition, the bedstead may, of course, include a head frame, a foot frame and other accessories.

In the above embodiments, the bed and the retaining device is used for medical treatment. However, it is, of course, possible to utilize the present invention at home for nursing a baby, caring for elderly people, and the like.

It must be understood that the invention is in no way limited to the above embodiments and that many changes may be brought about therein without departing from the scope of the invention as defined by the appended claims.

What is claimed is:

1. For use with a medical bed having a bed plate on which a patient is laid, a device for retaining the patient in a desired posture, comprising:

blocking means to be fitted on the bed plate for blocking motion of the patient along the bed plate; and fitting means for adjustably fitting the blocking means to the bed plate to adapt the blocking means for the desired posture of the patient, said fitting means comprising a suction pad arranged on said blocking means.

2. The retaining device of claim 1, wherein said blocking means includes an elongated member.

3. The retaining device of claim 1, wherein said elongated member is a pole which can stand substantially perpendicular to the bed plate.

4. The retaining device of claim 1, wherein said blocking means further comprises shock absorbing means for softening the impact when a patient bears against said blocking means.

5. The retaining device of claim 4, wherein said shock absorbing means includes a cushion provided on an outer periphery of said blocking means.

6. A medical bed comprising:

a bed plate on which a patient is laid in a desired posture; and means for adjustably retaining the patient in the desired posture in such a manner that the patient is prevented from moving along said bed plate, the retaining means comprises:

blocking means to be fitted on said bed plate for blocking motion of the patient along said bed plate; and fitting means for removably fitting said blocking means to said bed plate at an appropriate position to adapt said blocking means for the desired posture of the patient, and so that said blocking means fitted on said bed plate maintains said appropriate position, in which said fitting means can be operated by simply placing said blocking means on said bed plate at said appropriate position, and whereby said blocking means is firmly positioned in said appropriate position.

7. The medical bed of claim 6, wherein said fitting means includes:

a pole-like portion fixedly provided on the blocking means; and a plurality of recesses provided on the bed plate, each of the recesses being adapted to receive the pole-like portion so as to removably fit and firmly position the blocking means on the bed plate, and the recesses being dispersedly located on the bed plate so that a recess to receive the fitting means can be appropriately selected from said plurality of recesses for adapting the blocking means to the desired posture of the patient.

8. The medical bed of claim 7, wherein there are a greater number of said recesses than there are of said blocking means and said fitting means.

9. The medical bed of claim 8, wherein said recesses are formed in a two-dimensional array of equally-spaced recesses.

10. The medical bed of claim 9, wherein said blocking means has a first cross-sectional area, said fitting means having a cross-sectional area smaller than said blocking means, and said recess having a cross-sectional area approximately equal to the cross-sectional area of said fitting means such that said fitting means can be received within one of said recesses, and said blocking means received on said bed plate.

11. The medical bed of claim 7, wherein said blocking means has a cylindrical outer peripheral surface for contacting a patient, said outer peripheral surface being centered on an axis of said recess.

12. The medical bed of claim 7, wherein the blocking means includes an elongated member which is formed substantially co-linearly with the pole-like position and can stand on the bed plate substantially perpendicularly to the bed plate.

13. The medical bed of claim 12, wherein each of said recesses has a cylindrical shape, and said pole-like portion is a cylindrical bar which can be fitted in any one of said recesses.

14. The medical bed of claim 12, wherein each of said recesses and said pole-like portions have substantially the same regular polygonal cross-sectional shape in a plane taken along said bed plate.

15. The medical bed of claim 12, wherein the number of said recesses is larger than that of said pole-like portions, and the number of said pole-like portions is the same as that of said elongated members.

16. The medical bed of claim 7, wherein said recesses are regularly disposed to be at appropriate intervals between each other.

17. The medical bed of claim 7, wherein said blocking means further includes shock absorbing means for softening the impact when a patient bears against said blocking means.

18. The medical bed of claim 17, wherein said shock absorbing means includes a cushion provided on an outer periphery of said blocking means.

* * * * *